(12) United States Patent
Allardt et al.

(10) Patent No.: US 8,637,712 B2
(45) Date of Patent: Jan. 28, 2014

(54) PREVENTION OF PRECIPITATION FROM NITRATED AROMATIC CRUDE PRODUCTS

(75) Inventors: Holger Allardt, Schwarzheide (DE); Andreas Raichle, Ludwigshafen (DE); Reiner Reetz, Schwarzheide (DE); Johannes Büttner, Ruhland (DE); Michael Zöllinger, Eislingen (DE); Stefanie Haase, Bretnig-Hauswalde (DE); Rüdiger Fritz, Bernsdorf (DE)

(73) Assignee: BASF SE, Ludwigshafen (DE)

( * ) Notice: Subject to any disclaimer, the term of this patent is extended or adjusted under 35 U.S.C. 154(b) by 61 days.

(21) Appl. No.: 13/362,607

(22) Filed: Jan. 31, 2012

(65) Prior Publication Data
US 2012/0197047 A1    Aug. 2, 2012

Related U.S. Application Data

(60) Provisional application No. 61/437,726, filed on Jan. 31, 2011.

(51) Int. Cl.
*C07C 205/20* (2006.01)

(52) U.S. Cl.
USPC .................................... 568/711; 568/708

(58) Field of Classification Search
USPC .................................. 568/708, 711
See application file for complete search history.

(56) References Cited

U.S. PATENT DOCUMENTS

| | | | | | |
|---|---|---|---|---|---|
| 4,229,595 | A | * | 10/1980 | Bengtsson et al. | 568/706 |
| 4,814,518 | A | * | 3/1989 | Gossel et al. | 568/708 |
| 5,762,802 | A | * | 6/1998 | Carr et al. | 210/626 |
| 2005/0121160 | A1 | * | 6/2005 | Jetten et al. | 162/81 |
| 2007/0043244 | A1 | * | 2/2007 | Buettner | 568/708 |
| 2011/0130596 | A1 | | 6/2011 | Macht et al. | |
| 2011/0284391 | A1 | | 11/2011 | Fritz et al. | |
| 2011/0295039 | A1 | | 12/2011 | Raichle et al. | |
| 2011/0306795 | A1 | * | 12/2011 | Mackenroth et al. | 564/411 |

FOREIGN PATENT DOCUMENTS

| | | | | |
|---|---|---|---|---|
| GB | 1031450 | | 10/1964 | |
| GB | A-1031450 | * | 6/1966 | C07C 79/00 |

OTHER PUBLICATIONS

U.S. Appl. No. 13/421,453, filed Mar. 15, 2012, Waters, et al.
U.S. Appl. No. 13/311,371, filed Dec. 5, 2011, Haase, et al.
U.S. Appl. No. 13/759,466, filed Feb. 5, 2013, Raichle, et al.
International Search Report issued Aug. 6, 2012 in PCT/EP2012/051457.

* cited by examiner

*Primary Examiner* — Johann R Richter
*Assistant Examiner* — Pancham Bakshi
(74) *Attorney, Agent, or Firm* — Oblon, Spivak, McClelland, Maier & Neustadt, L.L.P.

(57) ABSTRACT

Precipitations of nitrohydroxyaromatic salts out of the nitrated crude products obtained in the nitration of aromatic compounds after alkaline scrubbing, for example mononitrotoluenes, are prevented by contacting the nitrated crude products with an acidic ion exchanger. The nitrated crude products are preferably selected from a feedstream to a distillation column, a bottoms circulation stream of a distillation column and a feedstream to a vaporizer.

9 Claims, 2 Drawing Sheets

PREVENTION OF PRECIPITATION FROM NITRATED AROMATIC CRUDE PRODUCTS

The present invention relates to a process for preventing precipitation of nitrohydroxyaromatic salts out of the nitrated crude products obtained in the nitration of aromatic compounds after alkaline scrubbing, and to a production plant for nitrating nitratable aromatic compounds.

The nitration of aromatic compounds is of great industrial significance since the aromatic nitro group can be converted easily to other functional groups. The nitration of aromatic compounds therefore has various uses, for example in the production of explosives, in the pharmaceutical industry, in the production of polymers, in the production of dyes and the like. The simplest and industrially most frequently used nitrating reagent is nitric acid/sulfuric acid mixtures (known as "nitrating acid") with variable ratios of the two acids. The concentrated sulfuric acid causes the formation of the actually active nitrile cation and additionally binds the water formed in the nitration process.

For example, mononitrotoluene (MNT) is prepared by nitration from toluene. The crude MNT obtained after removal of the nitrating acid also comprises nitrocresols, nitric acid, nitrogen oxides and other degradation products. The crude MNT is freed of the aforementioned impurities by scrubbing with water in several stages. In a first stage (acidic scrubbing), water is used to scrub out all strong acids, for example sulfuric acid, nitric acid and nitrous acid, or nitrogen oxides. In a second scrubbing stage (alkali scrubbing), an aqueous solution of a base, such as sodium carbonate solution or sodium hydroxide solution, is used to scrub out all weakly acidic substances, for example nitrocresols, picric acid and nitrobenzoic acids. In a last (neutral) scrubbing stage, water can be used to remove further amounts of impurities.

It has been found that the extraction of the nitrohydroxyaromatics, such as nitrocresols, into the aqueous phase is not quantitative. A portion of the nitrocresols remains dissolved in the nitroaromatics as nitrocresoxides. Water dissolved or dispersed in the organic phase enhances this effect. The purification of nitroaromatics, for example by distillation, or storage, can result in the crystallization of the nitrocresoxides. In the course of distillation, the nitrocresoxides are first concentrated, and can then crystallize out on vessel walls and pipelines. In the course of prolonged storage too, the nitrocresoxides can crystallize out. Since nitrocresoxides are unstable compounds which are explosive in pure form, mechanical or thermal stimulation can result in an unwanted explosion. Such explosions can also serve as an initial ignition and lead to detonation of the majority of nitroaromatics in contact therewith.

Similar problems as have already been described above in connection with the nitration of toluenes can also occur in the nitration of other nitratable aromatics with nitrating acid, for example in the preparation of nitrobenzenes. Nitrophenols or nitrophenoxides can be concentrated in the course of distillation and crystallize out on vessel walls and pipelines.

It is an object of the invention to specify a process for preventing potentially hazardous precipitation of the nitrated crude products obtained in the nitration of aromatic compounds after alkaline scrubbing.

The object is achieved by a process for preventing precipitation of nitrohydroxyaromatic salts from the nitrated crude products obtained in the nitration of aromatic compounds after alkaline scrubbing, which comprises contacting the nitrated crude products with an acidic ion exchanger.

In the context of the present invention, the term "nitratable aromatic compounds" is understood to mean especially benzene, toluene, xylenes, chlorobenzene, dichlorobenzenes, mononitrobenzene, mononitrotoluenes, mononitrochlorobenzene, dinitrotoluenes, etc. Benzene and toluene are preferred.

The nitration is effected in a manner known per se. It is performed preferably at temperatures of 30 to 100° C., especially 30 to 70° C. and most preferably at 35 to 50° C. The nitrating acid used is a nitrating acid typically used in the nitration of aromatics. The nitrating acid, a mixture of sulfuric and nitric acid, generally has a nitric acid content of 0.5 to 40% by weight, preferably 25 to 36% by weight. The molar ratio of nitratable aromatic compounds to nitric acid is preferably 1:1 to 1:1.3, more preferably 1:1.02 to 1.1.2.

After removal of the nitrating acid phase (i.e. of the acidic aqueous phase), the nitrated crude products are subjected to scrubbing with water. The scrubbing can be configured as a single-stage or multi-stage extraction process, which is performed as a liquid/liquid extraction. The extraction process may comprise, for example, a crosscurrent extraction, a countercurrent extraction or combinations thereof.

The nitrated crude products are subsequently subjected to a further purification. This is effected by means of alkaline and optionally subsequent neutral scrubbing, which may in turn optionally be followed by drying of the nitrated products.

Useful bases in the alkaline scrubbing are aqueous solutions or slurries of alkali metal (hydrogen)carbonates, alkali metal hydroxides, alkaline earth metal (hydrogen)carbonates or alkaline earth metal hydroxides, such as sodium carbonate, sodium hydrogencarbonate, sodium hydroxide solution or milk of lime. Aqueous solutions of sodium carbonate are generally preferred.

The nitration typically affords mixtures of nitrated aromatic compounds with different degrees of nitration, i.e. mixtures of mono-, di- and/or polynitrated aromatic compounds. When the nitrated representatives exhibit regioisomerism, mixtures of regioisomers are generally obtained.

In a preferred embodiment, the nitrated crude products comprise at least 85% by weight of mononitrotoluenes.

A typical crude MNT composition (technical-grade MNT), as can be prepared by nitration of toluene and subsequent alkaline scrubbing, is:

56 to 61% by weight, frequently 58.5 to 59.5% by weight, of o-nitrotoluene (NT),
4.0 to 4.5% by weight, frequently 4.1 to 4.3% by weight, of m-NT,
35 to 38% by weight, frequently 36.0 to 36.5% by weight, of p-NT,
0.3 to 0.8% by weight, frequently 0.4 to 0.7% by weight, of dinitrotoluene (DNT),
0.02 to 0.5% by weight, frequently 0.05 to 0.4% by weight, of water,
0.00001 to 0.2% by weight of toluene,
0.0001 to 0.05% by weight, frequently 0.0001 to 0.02% by weight, of different isomers of mono-, di- and trinitrocresoxides and
0 to 0.01% by weight of trinitrotoluene (TNT).

Depending on the pH values in the scrubbing operations, it is also possible for traces of mono-, di- and trinitrocresols to be present.

The nitrated crude products are typically separated by distillation according to their boiling point. The separation and purification are effected generally by single- or multi-stage distillation in customary rectification columns. Appropriately, the feed stream to be separated is introduced into the side of the column at a point between the column top and column bottom. A desired product of value can, according to the relative positions of the boiling points of the components to be separated and the purity requirements, for example, be obtained as a top product, side draw in the rectifying section, side draw in the stripping section or bottom product.

The column(s) is/are provided with a bottom heater, which may be configured internally or preferably externally with natural circulation or preferably forced circulation (via a pump).

One possible separation of the nitrated crude products is described hereinafter using the example of a crude MNT. The crude MNT can be fed into the side of an o-nitrotoluene column, low boilers being removed from the top thereof. At a suitable point in the rectifying section, the o-NT product of value is withdrawn in liquid form in a side draw. The bottom product of the o-nitrotoluene column, which comprises a mixture of p-NT, m-NT and DNT, is introduced into the side of a second column, in the bottom of which a mixture of m-NT, p-NT and DNT is obtained. The top product of the second column comprises a main fraction of p-NT and m-NT. Condensed top product is introduced into the side of a third column in which a top product composed of m-NT and p-NT, and pure p-NT as the bottom product are obtained.

After distillative removal of o-NT in the o-nitrotoluene column, the result is typically a bottom product of composition:
0.2 to 1% by weight of o-NT,
7 to 13% by weight of m-NT,
86 to 90% by weight of p-NT,
1 to 2% by weight of DNT,
0.0002 to 0.5% by weight, frequently 0.001 to 0.03% by weight, of different isomers of mono-, di- and trinitrocresoxides and
in each case 0 to 0.01% by weight of toluene, TNT and water.

Depending on the pH values in the scrubbing operations, it is also possible for traces of mono-, di- and trinitrocresols to be present.

After distillative removal of a product stream rich in m-NT and p-NT in the MNT column, the result there is typically a bottom product of composition:
0.0001 to 0.1% by weight of o-NT,
2 to 4% by weight of m-NT,
82 to 87% by weight of p-NT,
10 to 13% by weight of DNT,
0.001 to 10% by weight, frequently 0.005 to 1% by weight, usually 0.01 to 0.05% by weight, of different isomers of mono-, di- and trinitrocresoxides and
in each case 0 to 0.01% by weight of toluene, TNT and water.

Depending on the pH values in the scrubbing operations, it is also possible for traces of mono-, di- and trinitrocresols to be present.

According to the invention, the nitrated crude products are contacted with an acidic ion exchanger. The stream involved is preferably one of nitrated crude products selected from a feed stream to a distillation column, a bottoms circulation stream of a distillation column, and a feed stream to a vaporizer. The arrangement of the ion exchanger unit in the bottoms circulation system is not critical; the ion exchanger unit may be arranged between column bottom and pump, between pump and heater or between heater and circulation inlet.

Before the inventive treatment with an acidic ion exchanger, the nitrated crude products comprise generally 0.0001 to 0.05% by weight, usually 0.0001 to 0.02% by weight, of nitrohydroxyaromatic salts.

The inventive treatment converts nitrohydroxyaromatic salts which have remained in the nitrated crude products in liquid/liquid extraction to the acid form, which exhibits sufficient solubility in the nitrated crude products and does not crystallize out in the course of distillation and/or storage.

The success of the inventive treatment can be monitored or checked by determining the content of alkali metal or alkaline earth metal ions in the streams treated. The content of alkali metal and alkaline earth metal ions in the crude products treated should be less than 0.1 mg/l.

Alternatively, spectroscopic determination of the content of nitrohydroxyaromatic salts is possible. For example, VIS spectroscopic measurements can be carried out within a wavelength range from 400 to 600 nm (the maximum absorption wavelength of sodium 2,6-dinitro-p-cresoxide is, for example, 464 nm). The measurement can be carried out, for example, as a comparative measurement upstream and downstream of the ion exchanger unit, or downstream of the ion exchanger unit after preceding calibration for the nitrohydroxyaromatic salts.

The ion exchanger used in accordance with the invention is a cation exchanger in acid form.

Useful cation exchangers include in principle all ion exchange materials, for example organic ion exchange resins or inorganic ion exchangers, which have acidic groups, generally sulfo groups. Frequently, these are particulate, moderately or highly crosslinked organic polymers, frequently based on polystyrene, which have a multitude of acidic groups on the surface of the polymer particles. The average concentration of the acidic groups is typically in the range from 1 to 15 meq/kg of ion exchange resin. The mean particle size of the ion exchanger particles is typically in the range from 0.1 to 4 mm, and larger or else smaller particle sizes may be suitable according to the dimensions of the ion exchanger arrangement. The polymer particles may, for example, be in gel form or have a macroporous structure.

Such ion exchangers are known and are supplied commercially, for example under the trade names Lewatit® K or Lewatit® S from LANXESS, e.g. Lewatit® K 2629; Amberjet®, Amberlyst® or Amberlite® from Rohm & Haas, e.g. Amberlyst® 35 dry; Dowex® from Dow Chemicals, e.g. Dowex® UPCOR® Mono C-600; Diaion® from Mitsubishi Chemical Corp., e.g. Diaion® SK1B; and also Zorbax® 300 SCX (silica-based cation exchanger) from Agilent Technologies Deutschland GmbH.

The contacting with the ion exchanger can be effected in any conceivable manner. It is possible to distribute an ion exchanger in the nitrated crude products and then to remove it, for example by decanting or filtering.

Preferably, the nitrated crude products are passed through a bed of an acidic ion exchanger. The ion exchanger is present in a fixed bed arranged in a column through which the stream is passed. The column is preferably arranged vertically, and the stream flows through in the direction of gravity or counter to gravity. The extent of the fixed bed in flow direction is preferably 2 to 15 times the (longest) diameter of the fixed bed. It is also possible to use several columns connected in series.

The specific flow rate SV, i.e. the ratio of average flow rate V (volume flow rate) with which the nitrated crude products are passed through the ion exchanger arrangement to the total volume of the ion exchanger in the ion exchanger arrangement (bed volume BV), is of minor importance and is typically in the range from 0.1 to 5 $h^{-1}$.

The temperature at which the treatment is effected is above the melting temperature of the nitrated products, typically in the range from 0 to 150° C., preferably in the range from 20 to 120° C.

After a period of operation, the ion exchanger is saturated. The ion exchanger can be regenerated by passing an acid over it, preferably sulfuric acid. After the regeneration, rinsing with water or ammoniacal water is appropriate. This is preferably accomplished in an integrated acid/wastewater system with a nitrating plant.

The present invention further provides a production plant for nitrating nitratable aromatic compounds, wherein the production plant comprises the following units:
a) a nitration unit for nitrating nitratable aromatic compounds,
b) arranged downstream in the production line from the nitration unit, a unit for performing an acidic scrubbing by means of extraction,
c) arranged downstream in the production line from the unit for performing the acidic scrubbing, a unit for performing alkaline scrubbing,
d) arranged downstream in the production line from the unit for performing the alkaline scrubbing, a unit for performing neutral scrubbing,
e) arranged downstream in the production line from the unit for performing the neutral scrubbing, a distillation unit comprising one or more distillation columns, and
f) in the feed to at least one distillation column and/or at least one bottoms circulation system of a distillation column, at least one ion exchanger unit for contacting nitrated crude products with an acidic ion exchanger.

The invention is illustrated in detail by the appended drawings and the examples which follow.

Figure 1:
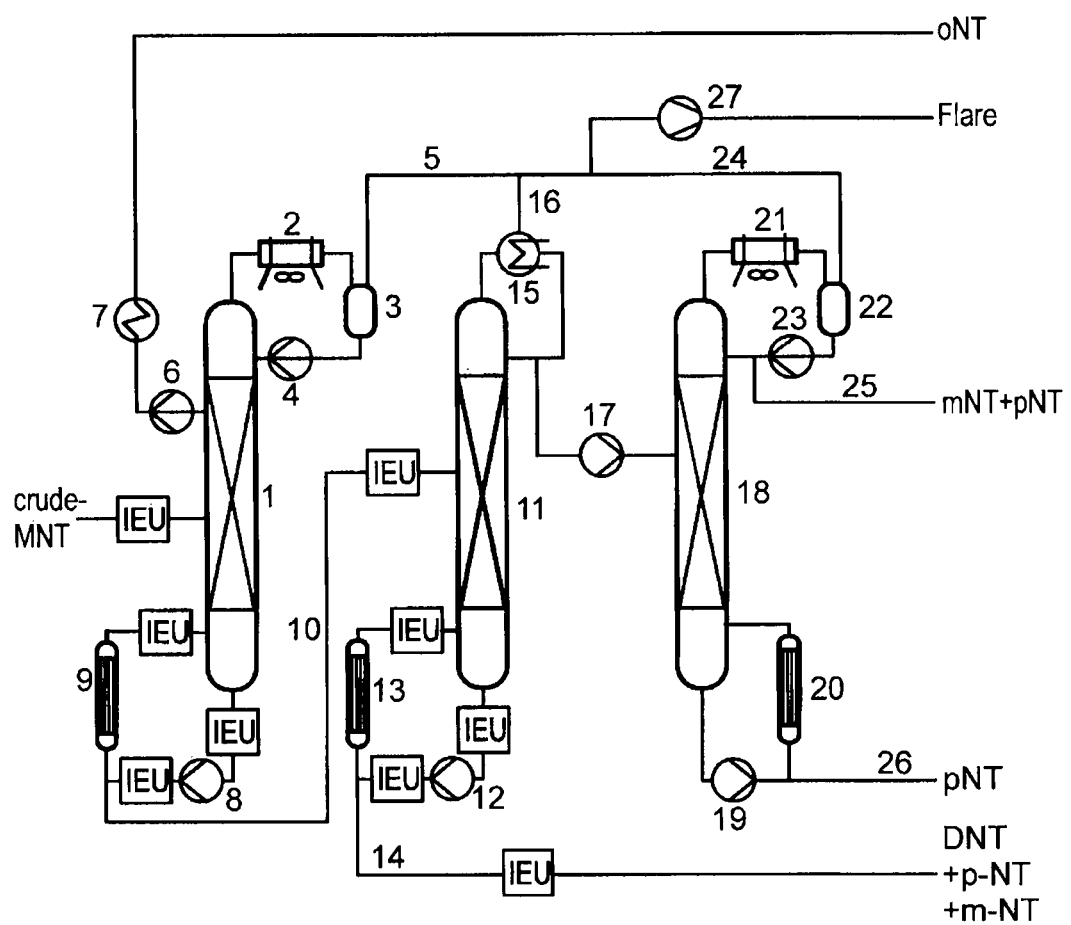
FIG. 1 shows a plant suitable for performance of the process according to the invention in the isomer separation of mononitrotoluene.

With regard to FIG. 1, the scrubbed crude MNT with a temperature of about 65° C. is fed by means of a pump (not shown) into column 1 below the middle. In column 1, a distillative separation is effected at a top pressure of 200 mbar and a bottom temperature of 187-189° C. The vacuum system 27 generates the distillation vacuum required. Low boilers drawn off via the top are partially condensed by means of an air cooler 2. A portion of the condensate passes via an intermediate vessel 3 and a pump 4 as reflux back to the top of the column 1. The uncondensed components are drawn off via line 5 and incinerated. Below the top of column 1, the o-NT product of value is drawn off with a temperature of about 162° C. via a side draw and the pump 6, cooled to about 60° C. in the heat exchanger 7 and pumped into an o-NT storage vessel (not shown).

A bottoms circulation pump 8 conveys the bottom product of the column 1, which consists essentially of a mixture of p-NT, m-NT and DNT, out of the bottom of column 1 via a falling-film evaporator 9; the energy input therein is effected by means of cooled 22 bar steam. The bottom product is discharged under quantitative control as a substream from the pressure side of pump 8 via line 10 to column 11.

The bottom product is fed into column 11 above the middle of column 11. The distillation is effected under a top pressure of 13 mbar and at a bottom temperature of 116-119° C. In the bottom of column 11, a mixture of m-NT, p-NT and DNT is obtained. The heat is introduced via the circulation system of a bottoms circulation pump 12 and a falling-film evaporator 13 (input flow from the top not shown in the diagram) which is operated with cooled 3.5 bar steam. The bottom draw rate via line 14 into a discharge vessel (not shown) is under level control. This establishes a DNT content of about 10-13%. The top product of column 11 comprising the majority of p-NT and m-NT is condensed in a heat exchanger 15 with hot water. The uncondensable components are drawn off via line 16 and incinerated. A portion of the condensate flows back to the top of column 11. The majority is drawn off by means of pump 17 and fed into column 18. The top product removal at a monitored rate from column 11 into column 18 regulates the temperature in the region of the top of column 11.

In column 18, the top product discharged from column 11 is fed in at a controlled rate below the upper third. The distillative separation is effected under a top pressure of 250 mbar. The bottom temperature is about 187-190° C. The level in the bottom of the column 18 is regulated by drawing off a substream of the pNT product on the pressure side of the bottoms circulation pump 19. Using this pump, the larger stream is heated with cooled 19.5 bar steam by means of a falling-film evaporator 20 and used to heat the bottom of column 18. The p-NT product of value is removed via line 26. The top product, which consists essentially of a mixture of m-NT and p-NT, is condensed in an air cooler 21; a substream is recycled via an intermediate vessel 22 and a pump 23 to the top of column 18. The uncondensable components are drawn off via line 24 and incinerated. The isomer mixture discharged via line 25 can, for example, be separated further by crystallization or used as an isomer mixture, optionally together with the bottom product of column 11, for the preparation of DNT.

At least one of the positions designated IEU in FIG. 1, in accordance with the invention, an ion exchange unit is provided, in order to contact the particular stream with an acidic ion exchanger.

Figure 3:
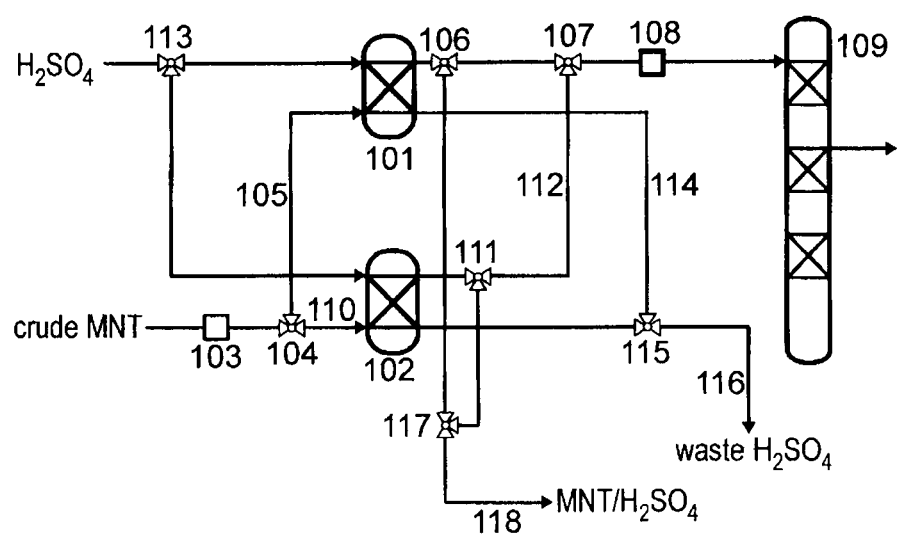
FIG. 3 shows an arrangement for a continuous treatment of a nitrated crude product with two parallel ion exchanger units.

With reference to FIG. 3, a crude MNT stream is passed through a VIS analysis point 103, which determines a reference value for the nitrocresoxide content. The three-way valve 104 is adjusted such that the crude MNT stream is conducted via line 105 to the ion exchange column 101, and flows through it from the bottom upward. The three-way valves 106 and 107 are set such that the treated MNT stream is conducted through the VIS analysis point 108 to the distillation column 109. Comparison of the measurement found at analysis point 108 with the reference value for the nitrocresoxide content can be used to check the success of the ion exchanger treatment. As soon as the ion exchanger in column 101 is exhausted, the three-way valves 104 and 107 are switched, and the crude MNT stream now flows via the three-way valve 104 to the ion exchange column 102, flows through it from the bottom upward and flows through the three-way valves 111 and 107 to the VIS analysis point 108 and the distillation column 109. Column 101 can then be regenerated by conducting in sulfuric acid via the three-way valve 113. Spent sulfuric acid can be discharged via line 114, three-way valve 115 and line 116. After regeneration has ended, sulfuric acid is displaced in column 101 by crude MNT, which is conducted in via line 105; the MNT/sulfuric acid mixed phase is removed via three-way valve 106, 117 and line 118. In a similar manner, it is possible to regenerate ion exchange column 102, by conducting sulfuric acid through the three-way valve 113 to column 102 and discharging it via three-way valve 115 and line 116. After regeneration has ended, sulfuric acid in column 102 is displaced by crude MNT, which is conducted in via line 110; the MNT/sulfuric acid mixed phase is removed via three-way valves 111, 117 and line 118.

EXAMPLES

Example 1

In a nitrogen-inertized 1000 mL three-neck flask, 0.1% by weight of Amberlyst® 35 dry (acidic ion exchanger from Rohm & Haas) was added to 500 g of MNT (0.01% by weight of o-NT, 2.7% by weight of m-NT, 85.8% by weight of p-NT, 11.5% by weight of DNT, 0.023% by weight of different isomers of mono-, di- and trinitrocresoxides and in each case <0.01% by weight of toluene, TNT and water) while stirring, and the mixture was stirred at 120° C. at ambient pressure. In order to be able to monitor the ion exchange, samples were taken at intervals of 10 min and analyzed for the sodium content with the aid of ICP-AES. Analysis showed no detectable traces of sodium after 40 min. In the course of this, the MNT mixture changed color from deep red to yellowish and clear. After filtration, Na-free MNT was obtained.

Example 2

The procedure was exactly as in example 1, except that 1% by weight of ion exchanger was used. As early as after 20 min, no sodium was detectable any longer.

Example 3

The procedure was exactly as in example 1, except that 5% by weight of ion exchanger was used. As early as after 10 min, no sodium was detectable any longer.

Example 4

The procedure was exactly as in example 1, except that DNT with a nitrocresoxide content of 300 ppm was used. After 40 min, no sodium was detectable any longer.

Example 5

Figure 2:
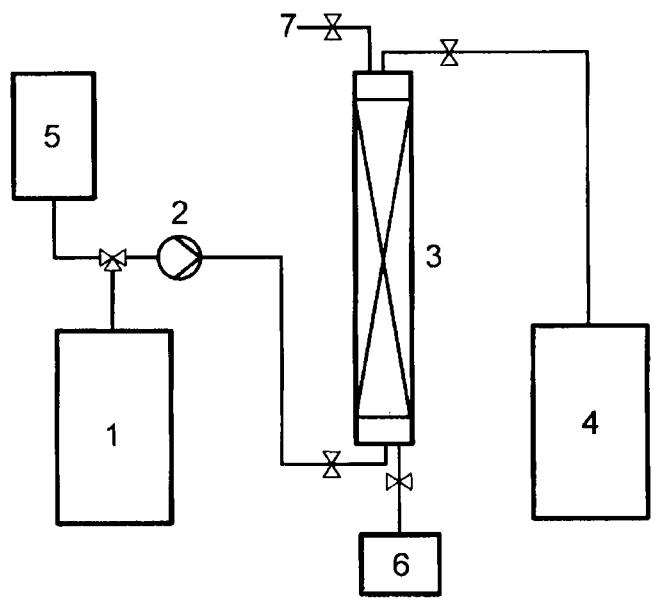
FIG. 2 shows an arrangement for batchwise treatment of a nitrated crude product with an acidic ion exchanger.

An arrangement as shown in FIG. 2 was used. Amberlyst® 35 dry (capacity ≥5 eq. $H^+$/kg) was introduced into a glass tube 3 with an internal diameter of 5 cm and a length of 80 cm to a fill height of 55 cm, and the ion exchange resin beads were fixed with two frits. Subsequently, MNT at 100° C. was pumped from a reservoir vessel 1 via a pump 2 through the ion exchanger from below into a collecting vessel 4. The pump output was 10 kg/h and the starting concentration of sodium upstream of the ion exchanger was 25 ppm, and no sodium was detectable any longer downstream of the ion exchanger. In this way, 100 kg of MNT were treated continuously.

Example 6

The procedure was exactly as in example 5. After the treatment of 100 kg of MNT, the tube 3 was charged with 2 liters of 2N sulfuric acid from vessel 5 and filled completely. In the isolated state, the ion exchanger is regenerated at 80° C. for 20 min. Thereafter, the tube 3 is emptied into a collecting vessel 6 and evacuated at 100° C.

After the ion exchanger had been dried, as in example 5, MNT at 100° C. was again pumped through the ion exchanger beads with the aid of a pump. The pump output was 10 kg/h and the starting concentration of sodium upstream of the ion exchanger was 25 ppm; no sodium was detectable any longer downstream of the ion exchanger. In this way, 100 kg of MNT were treated continuously.

Example 7

The procedure was exactly as in example 5, except that DNT with a nitrocresoxide content of 300 ppm was used and the temperature was limited to 80° C. In this way, 100 kg of DNT were treated continuously. No sodium was detectable any longer in the 100 kg of DNT downstream of the ion exchanger.

The invention claimed is:

1. A process for preventing precipitation of a nitrohydroxyaromatic salt out of a nitrated crude product obtained in a nitration of an aromatic compound after alkaline scrubbing, the process comprising contacting the nitrated crude product with an acidic ion exchanger.

2. The process according to claim 1, wherein the nitrated crude product is passed through a bed of the acidic ion exchanger.

3. The process according to claim 1, wherein the nitrated crude product is selected from the group consisting of a feed stream to a distillation column, a bottoms circulation stream of a distillation column, and a feed stream to a vaporizer.

4. The process according to claim 1, wherein the contacting with the acidic ion exchanger is effected at a temperature of 0 to 150° C.

5. The process according to claim 1, wherein the nitrated crude product comprises not more than 0.5% by weight of water.

6. The process according to claim 1, wherein the nitrated crude product comprises a nitrohydroxyaromatic sodium salt.

7. The process according to claim 1, wherein the nitrated crude product comprises 0.0001 to 0.05% by weight of a nitrohydroxyaromatic salt.

8. The process according to claim 1, wherein the nitrated crude product comprises at least 85% by weight of a mononitrotoluene.

9. The process according to claim 8, wherein the nitrohydroxyaromatic salt is at least one selected from the group consisting of a mononitrocresoxide, a dinitrocresoxide, and a trinitrocresoxide.

* * * * *